US010729428B2

(12) United States Patent
Marczyk et al.

(10) Patent No.: US 10,729,428 B2
(45) Date of Patent: Aug. 4, 2020

(54) SUTURE DELIVERY AND/OR RETRIEVAL DEVICE

(71) Applicant: Covidien LP, Mansfield, MA (US)

(72) Inventors: Joanna Marczyk, Stratford, CT (US); Daniel Broom, Branford, CT (US); John Marini, Milford, CT (US)

(73) Assignee: Covidien LP, Mansfield, MA (US)

( * ) Notice: Subject to any disclaimer, the term of this patent is extended or adjusted under 35 U.S.C. 154(b) by 284 days.

(21) Appl. No.: 15/468,189

(22) Filed: Mar. 24, 2017

(65) Prior Publication Data
US 2017/0319202 A1 Nov. 9, 2017

Related U.S. Application Data

(60) Provisional application No. 62/332,584, filed on May 6, 2016.

(51) Int. Cl.
A61B 17/06 (2006.01)
A61B 17/04 (2006.01)
A61B 17/00 (2006.01)
A61B 17/34 (2006.01)

(52) U.S. Cl.
CPC .... *A61B 17/06161* (2013.01); *A61B 17/0469* (2013.01); *A61B 17/0482* (2013.01); *A61B 17/0487* (2013.01); *A61B 17/06061* (2013.01); *A61B 17/06128* (2013.01); *A61B 17/06166* (2013.01); *A61B 17/3421* (2013.01); *A61B 2017/00362* (2013.01); *A61B 2017/00867* (2013.01); *A61B 2017/0472* (2013.01); *A61B 2017/0479* (2013.01); *A61B 2017/06142* (2013.01); *A61B 2017/06176* (2013.01)

(58) Field of Classification Search
CPC .............. A61B 2017/06142; A61F 2002/0068
See application file for complete search history.

(56) References Cited

U.S. PATENT DOCUMENTS

| 4,185,636 | A |   | 1/1980 | Gabbay et al. |
| 5,147,374 | A | * | 9/1992 | Fernandez ............ A61F 2/0063 606/151 |
| 5,359,831 | A | * | 11/1994 | Brown .............. A61B 17/06133 53/430 |
| 5,366,460 | A | * | 11/1994 | Eberbach ........... A61B 17/0057 128/887 |
| 5,643,293 | A |   | 7/1997 | Kogasaka et al. |
| 5,799,788 | A |   | 9/1998 | Webb |
| 5,871,489 | A |   | 2/1999 | Ovil |

(Continued)

FOREIGN PATENT DOCUMENTS

| WO | 2010046895 A1 | 4/2010 |
| WO | 2015047656 A1 | 4/2015 |

OTHER PUBLICATIONS

European Search Report dated Aug. 29, 2017, issued in EP Appln. No. 17169641.

*Primary Examiner* — Alexander J Orkin

(57) ABSTRACT

A suture delivery device includes a base portion and a deployment portion extending from the base portion. The base portion defines a longitudinal axis. The deployment portion includes a plurality of petals extending along the longitudinal axis parallel to one another when the deployment portion is in a delivery position and extending radially outward from the longitudinal axis when the deployment portion is in a deployed position.

15 Claims, 8 Drawing Sheets

(56) References Cited

U.S. PATENT DOCUMENTS

| | | | | |
|---|---|---|---|---|
| 6,029,805 | A * | 2/2000 | Alpern | A61B 17/06138 206/227 |
| 6,425,924 | B1 * | 7/2002 | Rousseau | A61B 17/0057 606/151 |
| 6,746,458 | B1 * | 6/2004 | Cloud | A61B 17/04 602/41 |
| 7,235,042 | B2 * | 6/2007 | Vanden Hoek | A61F 2/2481 600/16 |
| 8,011,499 | B2 | 9/2011 | McHugh Karow et al. | |
| 2002/0013571 | A1 * | 1/2002 | Goldfarb | A61B 17/0469 606/1 |
| 2006/0095052 | A1 | 5/2006 | Chambers | |
| 2008/0009888 | A1 | 1/2008 | Ewers et al. | |
| 2008/0097479 | A1 | 4/2008 | Boehlke et al. | |
| 2008/0167519 | A1 * | 7/2008 | St-Germain | A61F 2/0063 600/37 |
| 2009/0228021 | A1 * | 9/2009 | Leung | A61B 17/06166 606/139 |
| 2010/0147708 | A1 | 6/2010 | McHugh Karow et al. | |
| 2010/0256611 | A1 * | 10/2010 | Hansen | A61B 17/0057 606/1 |
| 2011/0046667 | A1 * | 2/2011 | Culligan | A61B 17/06114 606/224 |
| 2013/0211451 | A1 | 8/2013 | Wales et al. | |
| 2013/0218174 | A1 | 8/2013 | Bjerken | |
| 2013/0226233 | A1 * | 8/2013 | D'Agostino | A61B 17/04 606/228 |
| 2014/0276986 | A1 | 9/2014 | Hoarau et al. | |

\* cited by examiner

SUTURE DELIVERY AND/OR RETRIEVAL DEVICE

CROSS-REFERENCE TO RELATED APPLICATIONS

This application claims the benefit of and priority to U.S. Provisional Patent Application No. 62/332,584 filed May 6, 2016, the entire disclosure of which is incorporated by reference herein.

BACKGROUND

Technical Field

The present disclosure relates to endoscopic procedures. More particularly, the present disclosure relates to delivery and retrieval devices for a plurality of sutures during an endoscopic procedure.

Background of Related Art

Various surgical procedures are now performed endoscopically. More particular, these minimally invasive procedures are performed through one or more incisions in the skin. An access port or other device may be used to facilitate receiving the instruments and other objects into a cavity of a patient. During a surgical procedure, it may be necessary to use a plurality of armed sutures within the patient. Individually introducing armed sutures into the patient is time consuming and may complicate a procedure.

To reduce the time spent delivering individual armed sutures during surgical procedures and/or to simplify a suturing procedure, it would be beneficial to have a device for delivering a plurality of sutures and/or retrieving the needles of the used plurality of sutures.

SUMMARY

Accordingly, a suture delivery device for delivering a plurality of sutures is provided. The delivery device includes a base portion defining a longitudinal axis, and a deployment portion extending from the base portion. The deployment portion includes a plurality of petals extending along the longitudinal axis parallel to one another when the deployment portion is in a delivery position. The plurality of petals extends radially outward from the longitudinal axis when the deployment portion is in a deployed position.

A method of delivering a plurality of sutures to a cavity of patient is also provided. The method includes accessing a cavity of a patient through an opening, and positioning a delivery device within the cavity through the opening when the delivery device is in a delivery position, wherein the delivery device include a plurality of sutures releasably secured thereto. The method further includes transitioning the delivery device from the delivery position to a deployed position to expose the plurality of sutures, and performing a suturing procedure.

BRIEF DESCRIPTION OF THE DRAWINGS

The accompanying drawings, which are incorporated in and constitute a part of this specification, illustrate embodiments of the disclosure and, together with a general description of the disclosure given above, and the detailed description of the embodiments given below, serve to explain the principles of the disclosure, wherein.

DETAILED DESCRIPTION OF THE DRAWINGS

Figure 1:
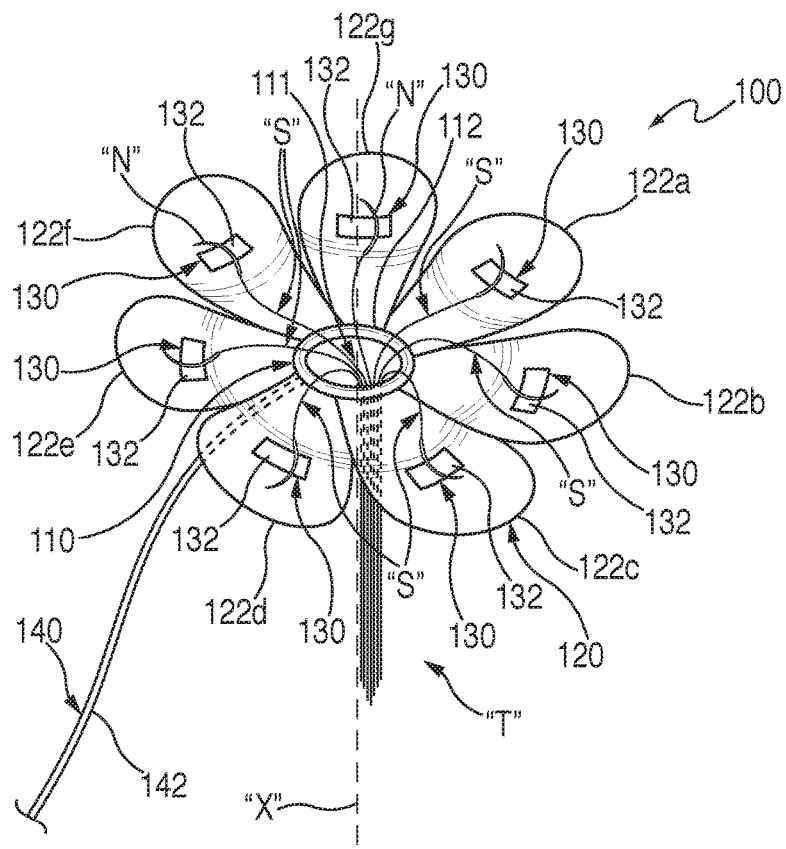
FIG. 1 is a perspective side view of a delivery device according to an embodiment of the present disclosure, in a deployed position.

Embodiments of the present disclosure will now be described in detail with reference to the drawings, in which like reference numerals designate identical or corresponding elements in each of the several views. As used herein, the term distal refers to the portion of the instrument or device which is farthest from the user, while the term proximal refers to that portion of the instrument or device which is closest to the user. In the following description, well-known functions or constructions are not described in detail to avoid obscuring the present disclosure in unnecessary detail.

As used herein with reference to the present disclosure, the terms laparoscopic and endoscopic are interchangeable and refer to procedures performed through a cannula or a small incision in the skin, and instruments for completing such procedures. It is believed that the present disclosure may find use in any procedure where access to the interior of the body is limited to one or more relatively small incisions, with or without the use of a cannula or other access port, as in minimally invasive procedures.

Embodiments of the present disclosure will be described with reference to the drawings. Although the embodiments will be shown and described as relates to the delivery of armed sutures "S" (FIG. 3), including a needle "N" (FIG. 3) and a thread "T" (FIG. 3) within a cavity "C" (FIG. 3) of a patient "P" (FIG. 3), and retrieval of the needle "N" and remaining thread "T" from the cavity "C" of the patient "P" following a suturing procedure, it is envisioned that the embodiments of the presently disclosed delivery devices may be used solely for delivery and/or solely for retrieval of one and/or more sutures "S", and that the suture(s) "S" may include multiple needles "N" or instead be unarmed. The thread "T" of the sutures "S" may be barbed, coated, formed of shape memory material, or be otherwise configured. It is understood that sutures "S" are available with needles "N" and thread "T" of various sizes, shapes, configurations, materials, and/or number, and that the embodiments of the present disclosure may be modified for use with any number of sutures having needle(s) and thread of any size, shape, configuration, and/or material.

Figure 2:
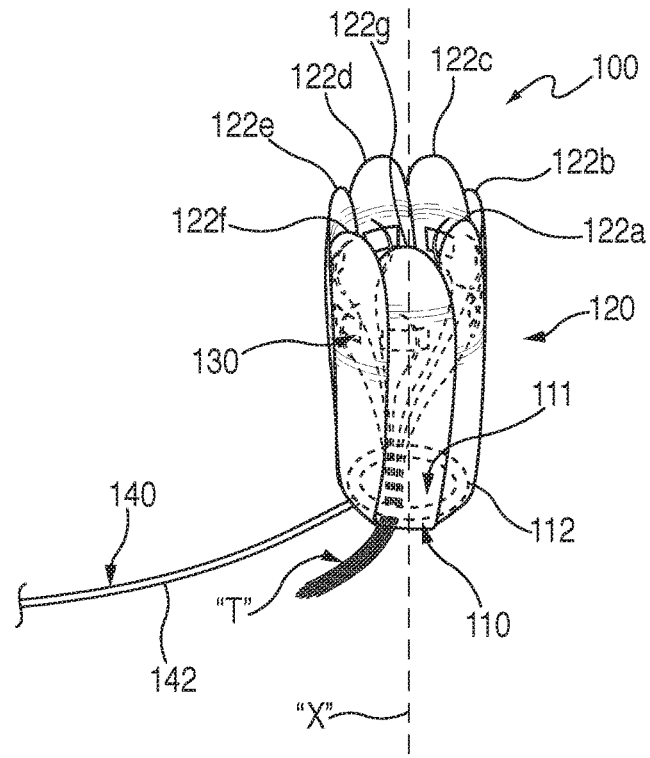
FIG. 2 is a perspective side view of the delivery device shown in FIG. 1, in a delivery position.
Figure 7:
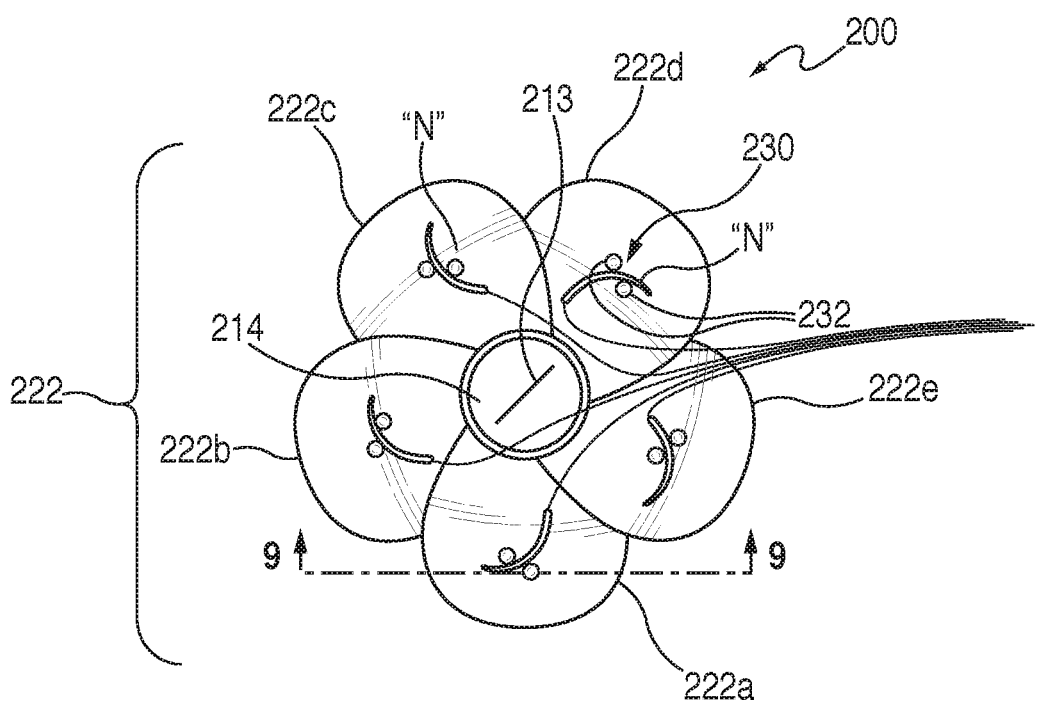
FIG. 7 is a top view of a delivery device according to another embodiment of the present disclosure, in a deployed position.

With reference now to FIGS. 1 and 2, a device for delivering and retrieving one or more sutures according to an embodiment of the present disclosure is shown generally as delivery device 100. The delivery device 100 includes a base portion 110, and a deployment portion 120 extending from the base portion 110. As will be described in further detail below, the base portion 110 and the deployment portion 120 may be integrally formed (FIG. 7) or secured to one another using know techniques. The base portion 110 provides structure to the delivery device 100 while the deployment portion 120 releasably retains one or more sutures "S".

Figure 16:
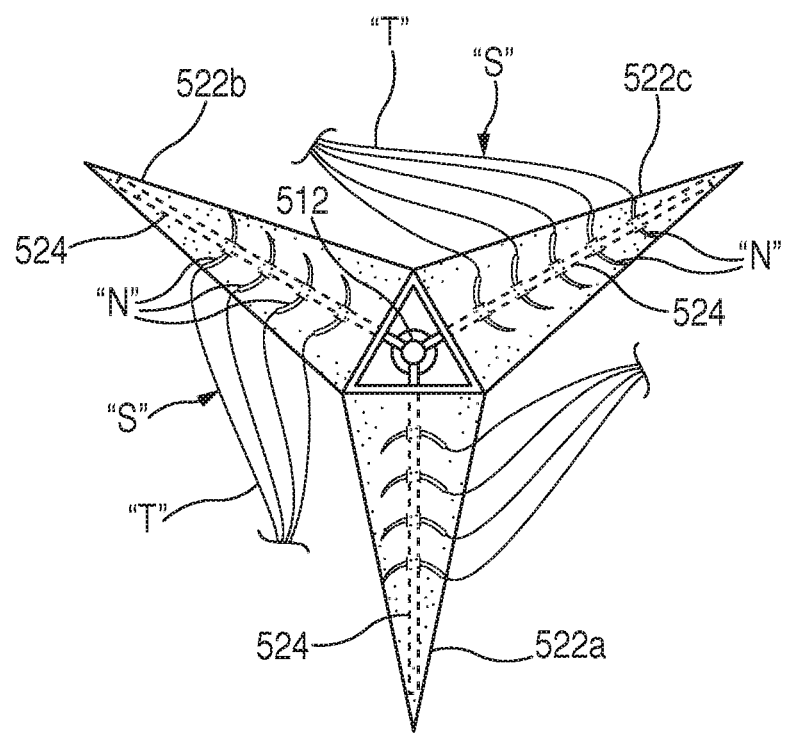
FIG. 16 is a top view of a delivery device according to another embodiment of the present disclosure, in a deployed position.

With continued reference to FIGS. 1 and 2, as shown, the base portion 110 of the delivery device 100 includes a support member or ring 112. Although shown as being circular, the support member 112 may include any suitable shape, including, for example, oval (FIG. 11), square (FIG. 13), and triangular (FIG. 16). As shown, the support member 112 defines an opening 111 therethrough. The threads "T" of the suture "S" may be received through the opening 111. The support member 112 may be solid (FIG. 12), or may include a cavity (FIG. 8) for receiving used needles "N". As will be described in further detail below, the support member 112 may formed of mesh or include a mesh or other suitable covering and/or coating for engaging used needles "N" following a suturing procedure.

Figure 3:
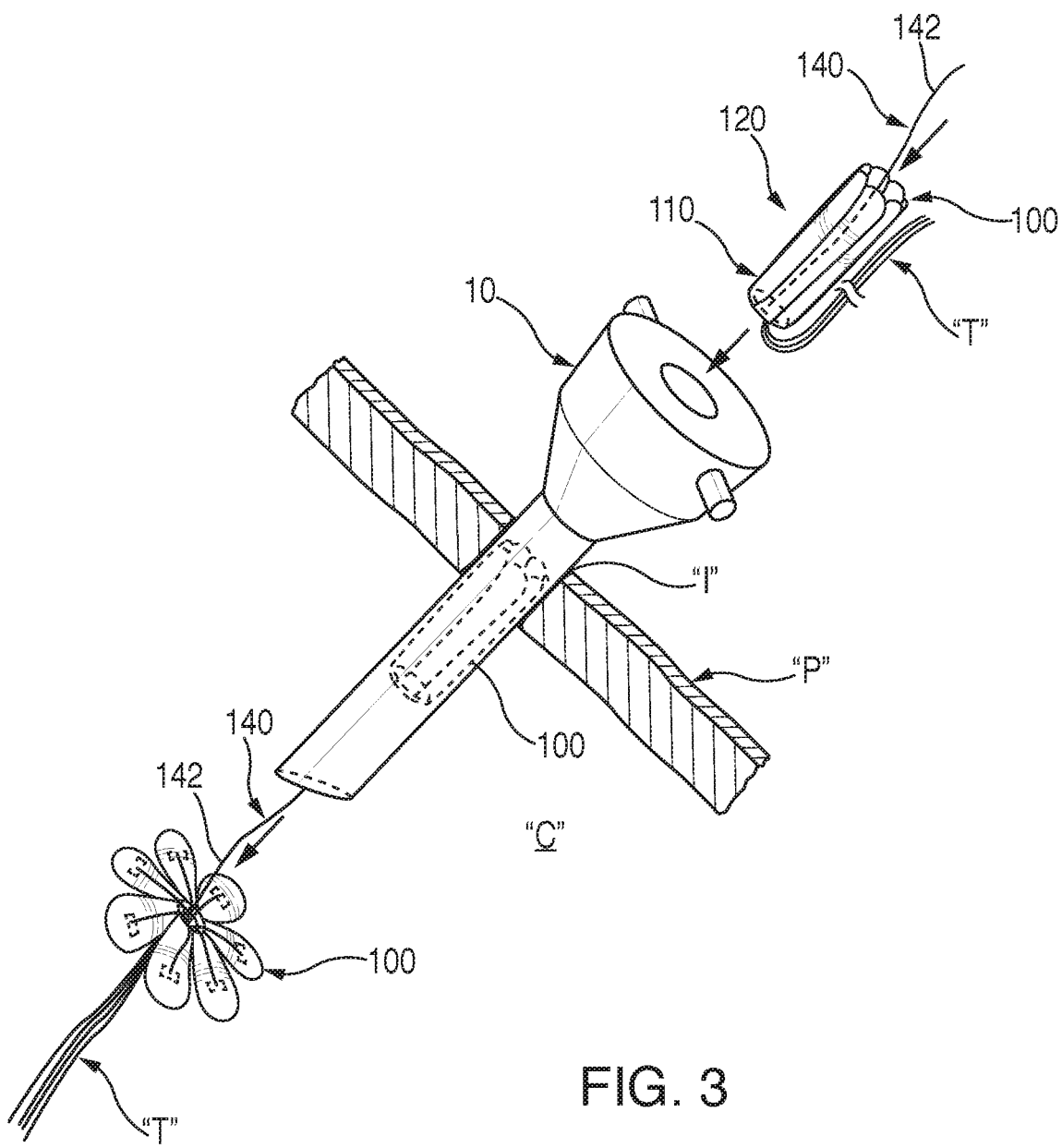
FIG. 3 is a schematic illustration of a delivery procedure using the delivery device shown in FIGS. 1 and 2.
Figure 6:
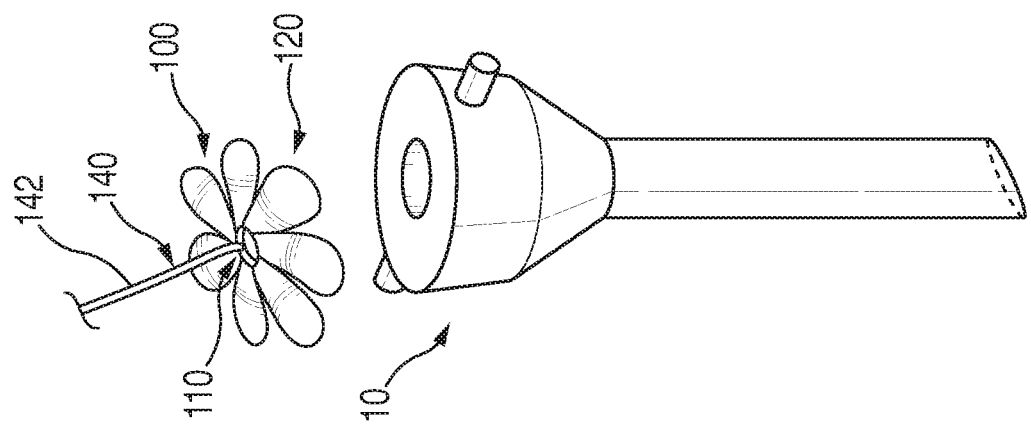
FIG. 6 is a schematic illustration of final step of the retrieval procedure of the delivery device shown in FIGS. 1 and 2.

The support member 112 of the delivery device 100 may be formed of plastic, polymer, metal, alloy, or other suitable material. It is envisioned that the support member 112 may be flexible to facilitate insertion of the delivery device 100 through an incision "I" (FIG. 3), with or without the use of an access assembly 10 (FIG. 3). In one embodiment, the support member 112 is formed of PTFE. Alternatively, the support member 112 is formed of a rubber material, e.g., a rubber stopper.

Figure 11:
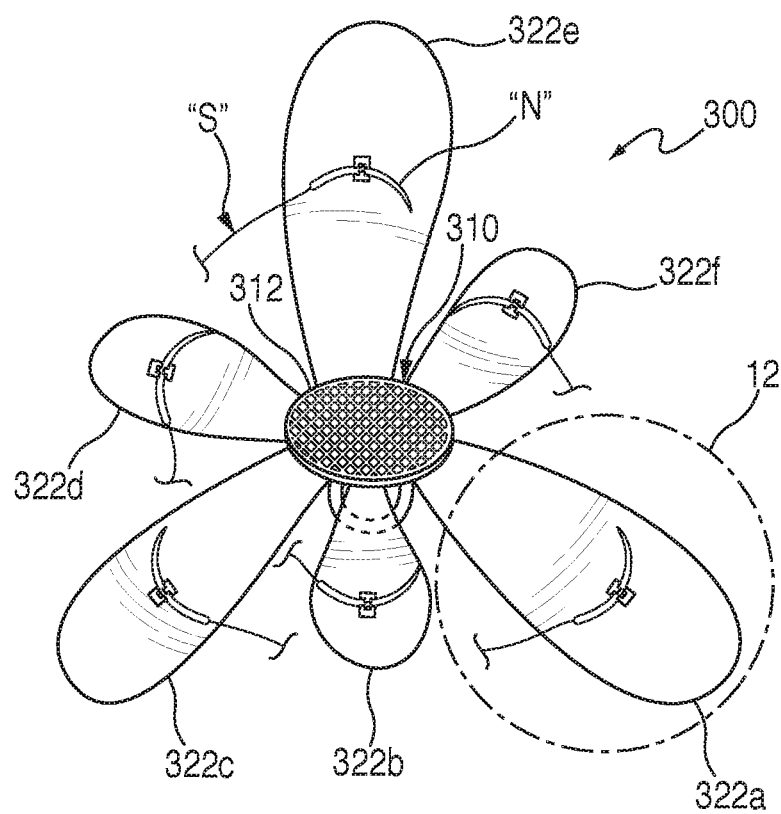
FIG. 11 is a perspective side view of a delivery device according to another embodiment of the present disclosure, in a deployed position.

The deployment portion 120 of the delivery device 100 includes a plurality of petals 122. Although shown including seven (7) petals 122a-g, it is envisioned that the deployment portion 120 of the delivery device 100 may include more or less than seven (7) petals 122, e.g., three (3) petals (FIG. 16), four (4) petals (FIG. 13), five (5) petals (FIG. 7), and six (6) petals (FIG. 11). Each of the petals 122a-g of the plurality of petals 122 may be substantially circular (FIG. 7), teardrop (FIG. 11), rectangular (FIG. 13), triangular (FIG. 16), or any other suitable shape. The petals 122a-g of the plurality of petals 122 may be of the same or different shape.

Each petal 122a-g of the plurality of petals 122 may be formed of thin plastic, fabric, or other suitable material. In embodiments, the plurality of petals 122 is formed of felt. Each of the petals 122a-g of the plurality of petals 122 may be solid, or may define a cavity 623 therein (FIG. 18) for receipt of a used needle "N". The support member 112 and the plurality of petals 122 may be formed of the same or different materials. As noted above the support member 112 and each petal 122a-g of the plurality of petals 122 may be integrally formed, e.g., monolithic, and/or secured to one other. In embodiments, the delivery device 100 is injection molded. The petals 122a-g of the plurality of petals 122 of the deployment portion 120 of the delivery device 100 may overlap, as shown. It is envisioned that each of the petals 122a-g of the plurality of petals 122 may instead be disposed about the support member 120 in contact with, or spaced from, adjacent petals.

Figure 17:
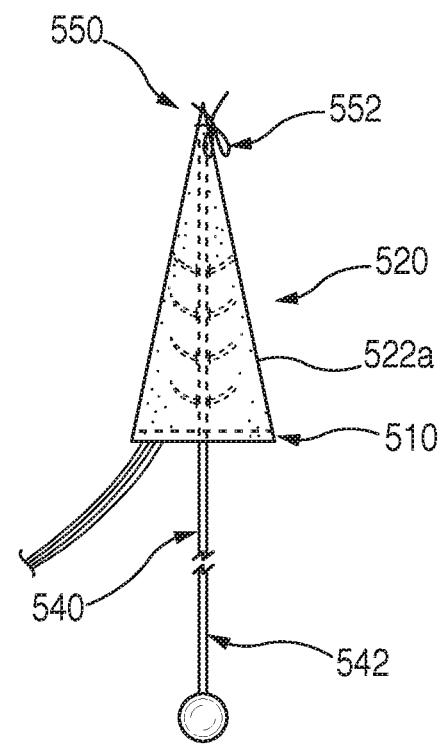
FIG. 17 is a side view of a delivery device shown in FIG. 16, in a delivery position.

The deployment portion 120 of the delivery device 100 is movable between a first or deployed position (FIG. 1) and a second or delivery position (FIG. 2). In the delivery position, each of the petals 122a-g of the plurality of petals 122 extend in a same longitudinal direction parallel to one another and to a central axis "x" of the delivery device 100, providing a compact configuration suitable for insertion through an incision "I" (FIG. 3) of a patient "P", with or without the use of an access port 10 (FIG. 3). The deployment portion 120 of the delivery device 100 may form a substantially cylindrical member, as shown, or may include a rounded configuration (FIG. 8) or a pyramid configuration (FIG. 17). Alternative configurations of the deployment portion 120 of the delivery device 100 may include cone, flower, umbrella, and shuttlecock.

Figure 5:
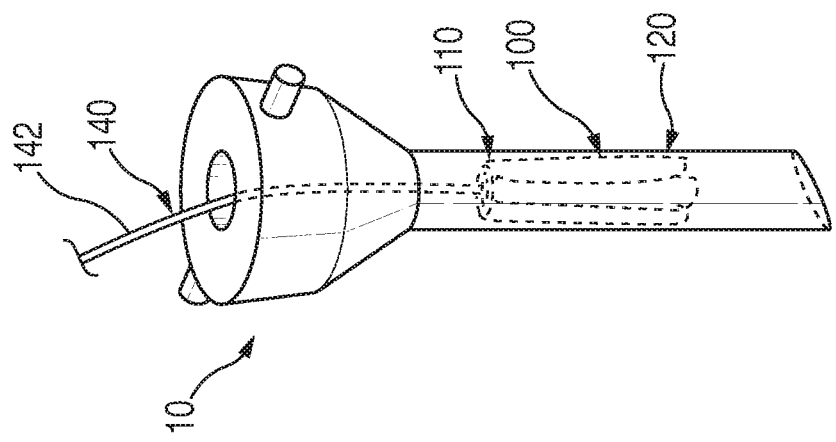
FIG. 5 is a schematic illustration of a subsequent step of the retrieval procedure of the delivery device shown in FIGS. 1 and 2.
Figure 4:
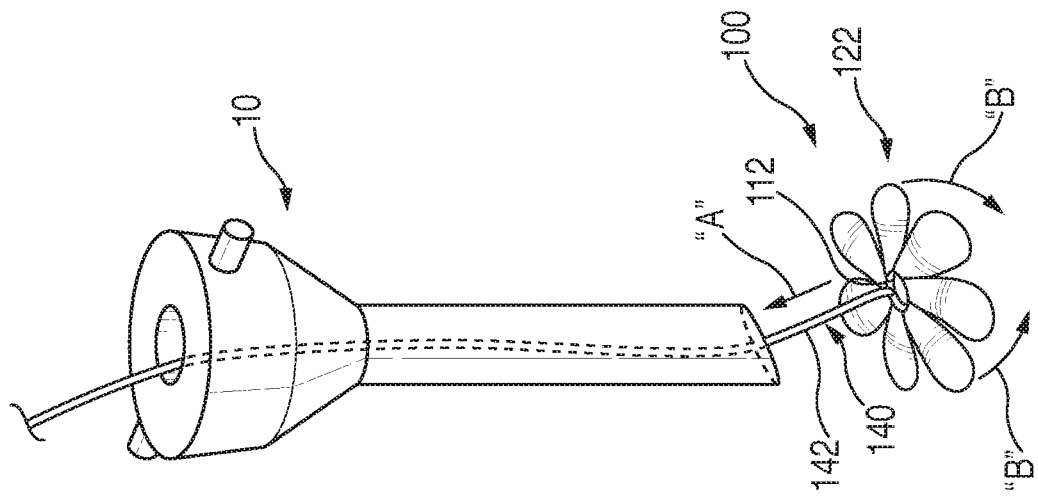
FIG. 4 is a schematic illustration of an initial step in a retrieval procedure of the delivery device shown in FIGS. 1 and 2.

When the plurality of petals 122 of the deployment portion 120 of the delivery device 100 are in the deployed position, each of the petal 122a-g of the plurality of petals 122 extend radially outwardly, thereby permitting access to an inner surface of the petals 122a-g. As will be described in further detail below, the delivery device 100 may further include a retrieval position (FIG. 5) in which each of the petal 122a-g of the plurality of petals 122 of the deployment portion 120 extend parallel to one another along the central axis "x" in a direction opposite to that in which each of the petals 122a-g of the plurality of petals 122 extend when the delivery device 100 is in the delivery position (FIG. 2). Alternatively, the delivery position and the retrieval position of the delivery device 100 may be the same.

Figure 13:
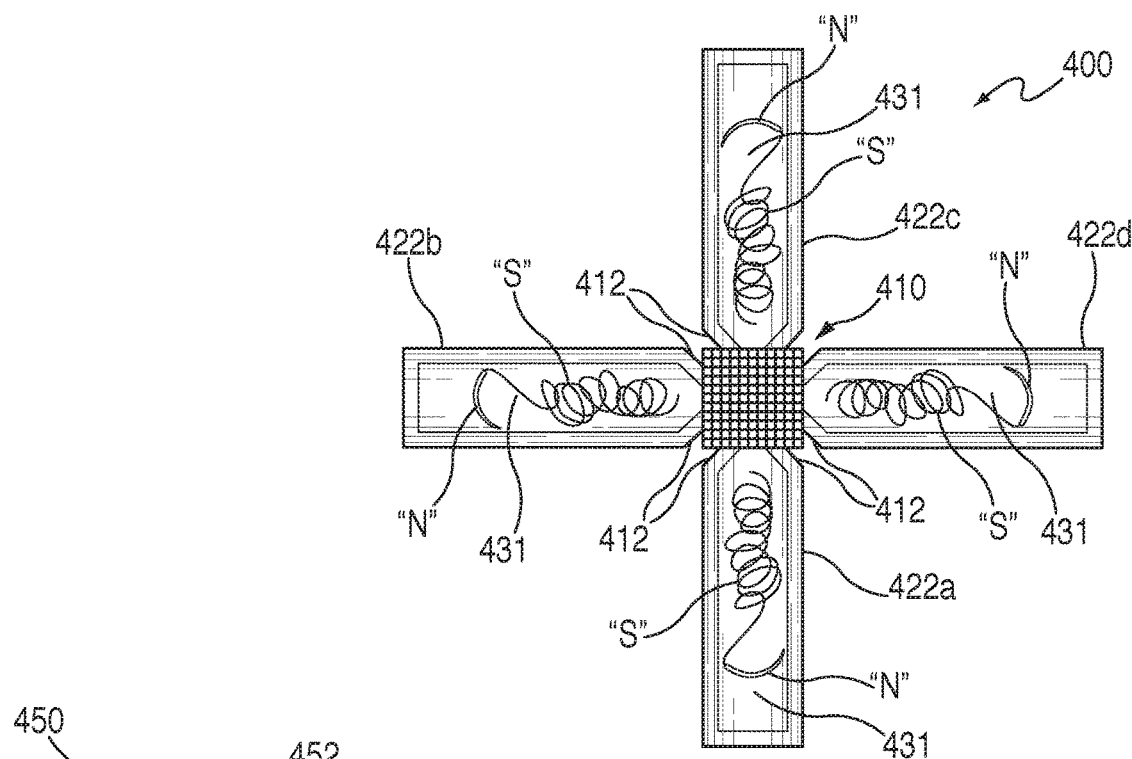
FIG. 13 is a top view of another delivery device according to another embodiment of the present disclosure, in a deployed position.

The petals 122a-g of the plurality of petals 122 of the deployment portion 120 of the delivery device 100 are each loosely secured to the support member 112 such that the plurality of petals 122 may freely move between the delivery position and the deployed position (and the retrieval position). Alternatively, each of the petals 122a-g of the plurality of petals 122 may be secured to the support member 112 by a hinge 412 (FIG. 13). The hinge may be configured to provide an opening force to move the plurality of petals 122 from the delivery position to the deployed position and/or from the deployed position to the delivery position. In embodiments, one or more of the petals 122a-g of the plurality of petals 122 includes a spring member (FIG. 16) for biasing the petals 122a-g from the delivery position to the deployed position and/or from the deployed position to the delivery position.

Figure 8:
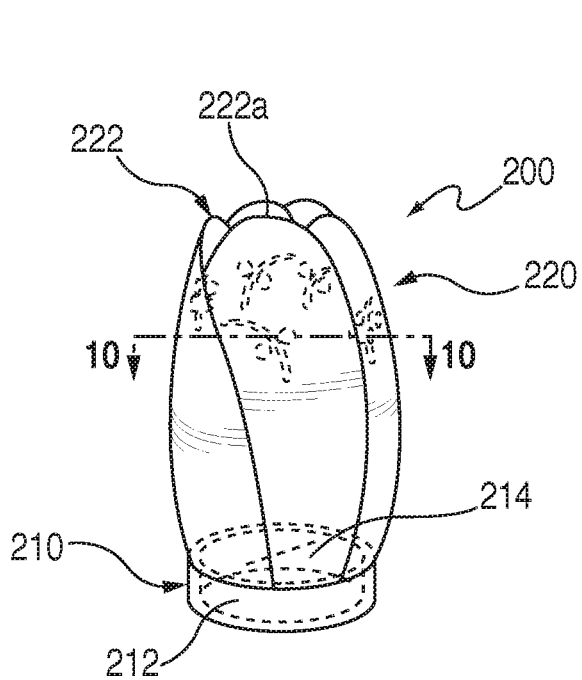
FIG. 8 is a side view of the delivery device shown in FIG. 7, in a delivery position.

It is envisioned that the deployment portion 120 of the delivery device 100 may include a securing mechanism, e.g., a strap (FIG. 5B), a sleeve (FIG. 14), a knot (FIG. 17), for maintaining the plurality of petals 122 in the delivery position (FIG. 2). Alternatively, each petal 122*a-g* of the plurality of petals 122 may be molded to have a first configuration (FIG. 9) when the delivery device 100 is in the deployed configuration (FIG. 7) and a second configuration (FIG. 10) when the delivery device 100 is in the delivery configuration (FIG. 8).

With continued reference to FIGS. 1 and 2, the deployment portion 120 of the delivery device 100 further includes a needle support 130 disposed on each petal 122*a-g* of the plurality of petals 122. As shown, the needle support 130 includes a pad member 132 secured to each petal 122*a-g* of the plurality of petals 122 for releasably retaining a needle "N" of suture "S" to each petal 122*a-g*. The pad members 132 may be formed of foam, rubber, or any other suitable biocompatible material. It is envisioned that the needle support 130 may include a pair or plurality of molded protrusions 232 (FIG. 7), a needle park 332 (FIG. 11), a recess (FIG. 13), or other any other suitable configuration for releasably retaining a needle "N".

Figure 15:
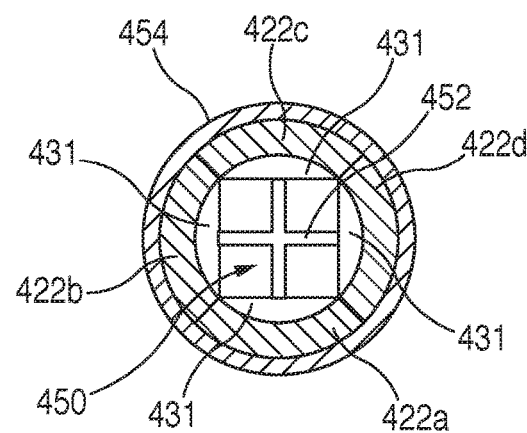
FIG. 15 is a cross-sectional end view of the petal delivery device shown in FIGS. 13 and 14, taken along line 15-15 in FIG. 14.

Alternatively, the material forming each of the petals 122*a-g* of the plurality of petals 122 of the deployment portion 120 of the delivery device 100 may include a pierceable material, e.g., fabric, mesh, through which a needle "N" may be received. In embodiments, the needles "N" may be secured directly to each of the petals 122*a-g* of the plurality of petals 122 using adhesive or other suitable material. In embodiments, the needle "N" is received within a recess (FIG. 15) defined by the petals. Although shown including only a single needle support 130 on each of petals 122*a-g* of the plurality of petals 122, it is envisioned that each of the petals 122*a-g* of the plurality of petals 122 may include a plurality of needle supports 130 of the same or different construction, for releasably retaining a plurality of needles "N".

Figure 14:
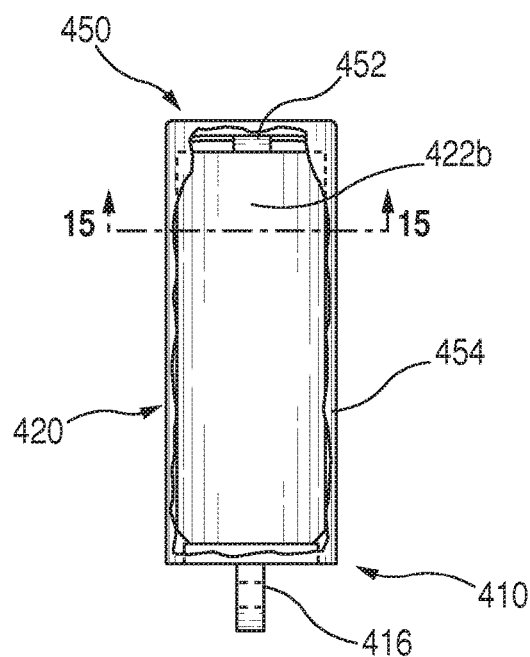
FIG. 14 is a side view of the delivery device shown in FIG. 13, in a delivery position.

The delivery device 100 further includes a retrieval mechanism 140. As shown, the retrieval mechanism 140 of the delivery device 100 includes a string or cord 142 secured to the support member 112. The delivery device 100 may instead include a rod (FIG. 17) or other elongate body (not shown) secured to the base portion 110 of the delivery device 100. The elongate body may also facilitate positioning of the delivery device 100 through an incision "I" (FIG. 3) and into a cavity "C" (FIG. 3) of a patient "P" (FIG. 3). Alternatively, the base portion 110 of the delivery device 100 may be configured for engagement by a surgical instrument (not shown), e.g., scope, or forceps, and the surgical instrument may be used to delivery and/or retrieve the delivery device 100. For example, the base portion 110 of the delivery device 100 may include a loop (FIG. 11) or a tab (FIG. 14). In embodiments, the base portion 110 is configured to be directly engaged by the surgical instrument.

Operation of the delivery device 100 will now be described with reference to FIGS. 3-6. Referring initially to FIG. 3, the delivery device 100 may be provided to a clinician with the sutures "S" previously attached to the petals 122*a-g* of the plurality of petals 122. Alternatively, the sutures "S" may be secured to the petals 122*a-g* of the plurality of petals 122 by the clinician. In this manner, the delivery device 100 may be loaded with only the suture "S" of a particular type(s) and of a certain number to complete a given suture procedure. As such, waste material may be limited, and unnecessary objects need not be introduced into the patient "P".

Once the needles "N" of the suture "S" are secured to the respective petals 122*a-g* of the plurality of petals 122, the plurality of petals 122 are moved to the delivery position.

The plurality of petals 122 may be provided to the clinician in the delivery position, or may be moved to the delivery position manually by the clinician. To maintain the plurality of petals 122 in the delivery position, the petals 122*a-g* may be secured to one another using a locking mechanism, such as a releasable adhesive, a sleeve, a strap or straps, clips, barbs, and/or knot or knots. In embodiments, the locking mechanism may be self-locking in that the locking mechanism naturally secures the petals upon interaction or contact with each other. Alternatively, the locking mechanism is manually manipulated to secure the petals to each other.

The locking mechanism may be disposed on any portion of at least one petal. In embodiments, the locking mechanism is disposed on a distal end of at least one petal, and may be disposed on a distal end of each of the petals. In other embodiments, the locking mechanism is disposed on a proximal end of at least one petal, and may be disposed on a proximal end of each of the petals.

As noted above, the delivery device 100 may be delivered through the incision "I" in a variety of ways. The delivery device 100 may be guided through the incision "I", with or without the access portion 10, using the end of a scope, forceps, or other suitable instrument. Alternatively, a rod or other member may be secured to the delivery device 100 to facilitate insertion of the delivery device through the incision "I".

Once the delivery device 100 has been delivered to the cavity "C" of the patient "P", the deployment portion 120 of the delivery device 100 is deployed. As shown, the deployment portion 120 of the delivery device 100 deploys automatically once the delivery device is no longer constrained by the access port 10. Alternatively, a strap(s) is(are) cut, a knot(s) is(are) untied, and/or a sleeve is removed or dissolved to permit the deployment of the deployment portion 120 of the delivery device 100.

During a suturing procedure, the sutures "S" may be removed from each of the petals 122*a-g* of the plurality of petals 122 as desired, and the suture "S" may be used in a traditional manner. The used needles "N" may be reattached to pad members 132 of the needle supports 130 on each of the petals 122*a-g* of the plurality of petals 122 to permit removal of the used needles "N" from the cavity "C" of the patient "P".

When all of the sutures "S" secured to the petals 122*a-g* are used, e.g., the delivery device 100 is empty, or upon completion of the suturing procedure, the delivery device 100 is removed from the cavity "C" of the patient "P". The delivery device 100 includes the retrieval mechanism 140, e.g., string 142, for pulling the delivery device 100 back through the incision "I". As the string 142 of the retrieval mechanism 140 is pulled in a proximal direction, as indicated by arrow "A" in FIG. 4, the petals 122*a-g* of the plurality of petals 122 move to the retrieval position, as indicated by arrows "B" in FIG. 4. As noted above, the retrieval position may be the same or opposite of the delivery position (FIG. 2).

Once the delivery device 100 is removed from the cavity "C" of the patient "P", the delivery device 100 may be disposed of in any traditional manner. It is envisioned that the delivery device 100 may be emptied of the used needles "N", reloaded with additional sutures, and reused during the same procedure, and/or the delivery device 100 may be emptied of used needles "N", sterilized, reloaded with additional sutures, and reused during subsequent procedures.

With reference now to FIGS. 7-10, a delivery device according to another embodiment of the present disclosure is shown generally as delivery device 200. The delivery device 200 is substantially similar to delivery device 100 described hereinabove, and will only be described in detail as relates to the differences therebetween.

The delivery device 200 includes a base portion 210 and a deployment portion 220 integrally formed with the base portion 210. The base portion 210 and the deployment portion 220 are formed of a molded plastic or polymer. The base portion 210 of the delivery device 200 forms a container 212 into which used needles "N" may be placed to facilitate removal of the needles "N" from the cavity "C" (FIG. 3) following a suturing procedure. The container 212 may include a lid 214 defining a slit 213 or other means for positioning a used needle "N' therein.

Figure 9:
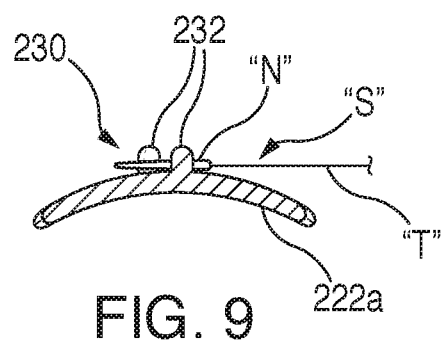
FIG. 9 is a cross-sectional end view of a petal of the delivery device shown in FIGS. 7 and 8, taken along line 9-9 in FIG. 7.
Figure 10:
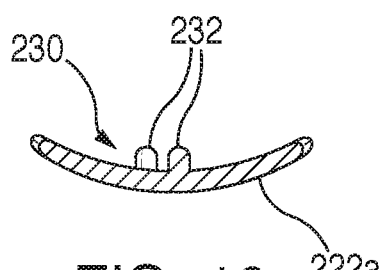
FIG. 10 is a cross-sectional top end view of a petal of the delivery device shown in FIGS. 7 and 8, taken along line 10-10 in FIG. 10.

The deployment portion 220 includes a plurality of petals 222. Each petal 222*a-e* of the plurality of petals 222 includes a needle support 230 in the form of a pair of protrusions 232 for releasably retaining sutures "S". Each of the petals 222*a-e* of the plurality of petals 222 of the deployment portion 220 of the delivery device 200 includes a first configuration when the deployment portion 220 is in a delivery position (FIG. 8) and when the deployment portion 220 is in a deployed position (FIG. 8). As shown in FIG. 9, the petals 222*a-e* of the plurality of petals 222 have a convex cross-sectional profile when the deployment portion 220 is in the deployed position, and as shown in FIG. 10, the petal 222*a-e* include a concave cross-sectional profile when the deployment portion 220 is in the delivery position. The petals 222*a-e* are configured such that when the deployment portion 220 is in the delivery position, the needle "N" on each of the petals 222*a-e* is readily accessible by the clinician. It is envisioned that the petals 222*a-e* may remain in either a convex or concave profile regardless of the delivery position, retrieval position, and/or deployment position.

It is envisioned that the needle support 230 of the delivery device 200 may be configured to securely retain the needles "N" when the deployment portion 220 of the delivery device 200 is in the delivery position, so as to prevent inadvertent separation of the needles "N" from the respective petals 222*a-f*. It is further envisioned in some embodiments, that when the deployment portion 220 is moved to the deployed position, the needle support 230 is configured to release or permit the release of the needles "N".

Figure 12:
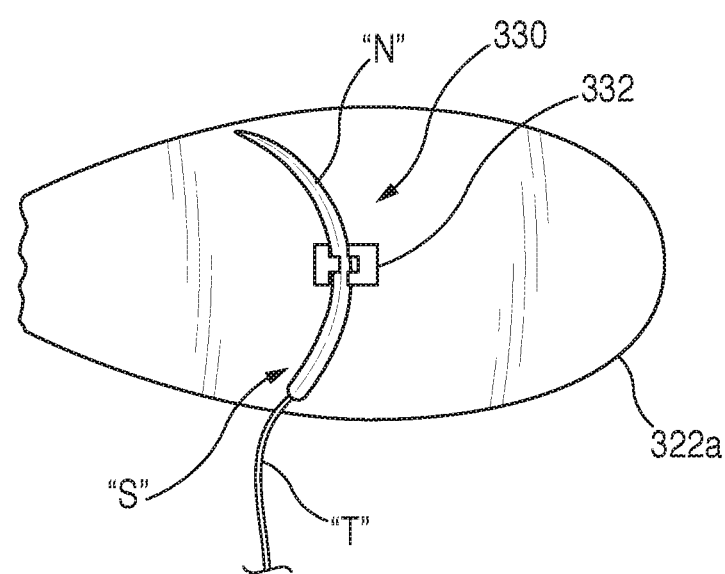
FIG. 12 is an enlarged view of the indicated area of detail shown in FIG. 11.

With reference now to FIGS. 11 and 12, a delivery device according to another embodiment of the present disclosure is shown generally as delivery device 300. The delivery device 300 is substantially similar to delivery devices 100, 200 described hereinabove, and will only be described in detail as relates to the differences therebetween.

The delivery device 300 includes a base portion 310 and a deployment portion 320 secured to the base portion 310. The base portion 310 of the delivery device 300 is formed of a material which can be is penetrated by the needles "N". In some embodiments, the base portion 310 is made from, or includes, a rubber material, e.g., a rubber stopper. The base portion 310 may be made from, or includes, a mesh cover 312 to which used needles "N" may be secured to facilitate removal of the needles "N" from the cavity "C" (FIG. 3) following a suturing procedure. The base portion 310 further includes a loop 314 extending distally therefrom for facilitating retrieval of the delivery device 300 from the cavity "C".

The deployment portion 320 of the delivery device 300 includes a plurality of petals 322. As shown, the petals 322*a-f* of the plurality of petals 322 are of different shapes and sizes, and may accommodate sutures "S" of different shapes and sizes. Each of the petals 322*a-f* includes a needle support 330 in the form of a needle park 332 for releasably retaining sutures With reference now to FIGS. 13-15, a delivery device according to another embodiment of the present disclosure is shown generally as delivery device 400. The delivery device 400 is substantially similar to delivery devices 100, 200, 300 described hereinabove, and will only be described in detail as relates to the differences therebetween.

The delivery device 400 includes a base portion 410 and a deployment portion 420 secured to the base portion 410 by a hinge 412. The hinge 412 permits movement of the deployment portion 420 between a deployed position (FIG. 13) and a retrieval position (FIG. 14). The hinge 412 may be integrally formed with either or both of the base portion 410 and the deployment portion 420, or may be secured therebetween. The hinge 412 may be passive, thereby allowing the deployment portion 420 to move between the deployed position and the delivery position or retrieval position without assistance, or the hinge 412 may be configured to bias the deployment portion 420 between the deployed position and the delivery or retrieval position. The base portion 410 further includes a loop 416 extending distally therefrom for facilitating retrieval of the delivery device 400 from the cavity "C".

The deployment portion 420 of the delivery device 400 includes a plurality of petals or sections 422. As shown, the petals 422*a-d* of the plurality of petals 422 each have a semi-circular cross-sections (FIG. 15) that, when the deployment portion 420 of the delivery device 400 is in the delivery position, the deployment portion 420 forms a substantially cylindrical body.

The deployment portion 420 of the delivery device 400 may be maintained in the delivery position by a release mechanism 450. The release mechanism 450 may include straps 452 secured to the petals 422*a-d* of the plurality of petals 422, or a sleeve 454 received about the petals 422*a-d*. It is envisioned that the sleeve 454 may be cut away or otherwise removed from about the deployment portion 420 of the delivery device 400. In embodiments, the sleeve 454 is dissolvable when contacted with a fluid and/or at a given temperature. Each of the petals 422*a-d* defines a recess 431 for receiving the sutures "S". An adhesive or other material may be used to releasably retain the sutures "S" within the recesses 431.

Following a suturing procedure, the used needles "N" may be placed back within the recesses 431 of the petals 422*a-d* to facilitate removal of the needles "N" from the cavity "C" of the patient "P".

With reference now to FIGS. 16 and 17, a delivery device according to another embodiment of the present disclosure is shown generally as delivery device 500. The delivery device 500 is substantially similar to delivery devices 100, 200, 300, 400 described hereinabove, and will only be described in detail as relates to the differences therebetween.

The delivery device 500 includes a base portion 510 and a deployment portion 520 secured to the base portion 510. The base portion 510 of the delivery device 500 is triangular, and includes an attachment member 512 for releasably securing a retrieval mechanism 540, e.g., an insertion/retrieval rod 542, thereto. The rod 542 may be releasably secured to the attachment member 512 of the base portion with a threaded connection, slot and tab configuration, friction fit, or in any other suitable manner.

The deployment portion 520 of the delivery device 500 includes a plurality of petals 522. As shown, the petals 522*a-c* of the plurality of petals 522 are of triangular in shape, and are formed of, or covered with, a fabric or other pierceable material through which one or more needles "N" may be positioned. Each of the petals 522a-c includes a spring member 524 for biasing the respective petals 522a-c to a deployed position (FIG. 16). Although the spring member 524 is shown as an elongate flexible member secured to the base portion 510 of the delivery device 500, it is envisioned that the spring member 524 may instead include a coil spring, a living hinge, or any other suitable biasing member.

The delivery device 500 includes a release mechanism 550, e.g., a knot 552 (FIG. 17) secured to the free ends of the petals 522a-c of the plurality of petals 522 to secure the deployment portion 520 of the delivery device 500 in a delivery position.

Figure 18:
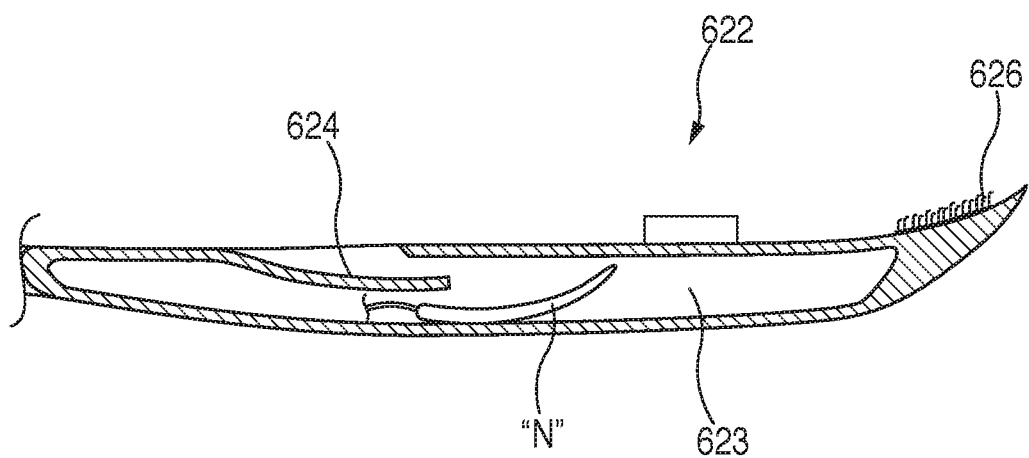
FIG. 18 is a cross-sectional side view of a petal of a delivery device according to another embodiment of the present disclosure.

With reference now to FIG. 18, in another embodiment of a delivery device according to the present disclosure, a petal 622 defines a cavity 623 for receiving one or more used needles "N" and/or thread "T" of the sutures "S". A flap or opening 624 provides access to the cavity 623 to permit placement of the needle "N" and/or thread "T" within the cavity 623.

The petal 622 may further include a trap member 626 formed on a free end thereof for trapping scrap material as the delivery device is removed from a patient "P" (FIG. 3). The trap member 626 may include an adhesive, or a Velcro®-like material for gripping the scrap material as the delivery device is removed from a patient. When the delivery device is in a retrieval positions, the ends of the petal 622 including the trap member 626 engage one another, furthering preventing trapping scrap material during retrieval of the delivery device. The trap member 626 may be configured to secure multiple petals 622 together when the delivery device is in the delivery position and/or the retrieval position.

Persons skilled in the art will understand that the devices and methods specifically described herein and illustrated in the accompanying drawings are non-limiting exemplary embodiments. It is envisioned that the elements and features illustrated or described in connection with one exemplary embodiment may be combined with the elements and features of another without departing from the scope of the present disclosure. As well, one skilled in the art will appreciate further features and advantages of the disclosure based on the above-described embodiments. Accordingly, the disclosure is not to be limited by what has been particularly shown and described, except as indicated by the appended claims.

What is claimed is:

1. A suture delivery device comprising:
   a base portion defining a longitudinal axis; and
   a deployment portion extending from the base portion, wherein the deployment portion includes,
      a plurality of petals extending along the longitudinal axis parallel to one another and in an overlapping arrangement with adjacent petals of the plurality of petals forming a cylinder when the deployment portion is in a delivery position and extending radially outward from and substantially perpendicular to the longitudinal axis when the deployment portion is in a deployed position; and
      a needle support on each petal of the plurality of petals, each of the needle supports being configured to support a suture needle, wherein when the deployment portion is in the delivery position the plurality of petals completely enclose the suture needles.

2. The suture delivery device of claim 1, wherein the base portion and the deployment portion are integrally formed.

3. The suture delivery device of claim 1, further including a release mechanism for maintaining the deployment portion in the delivery position.

4. The suture delivery device of claim 3, wherein the release mechanism includes a strap.

5. The suture delivery device of claim 3, wherein the release mechanism includes a sleeve received over the deployment portion.

6. The suture delivery device of claim 1, further including a retrieval mechanism for retrieving the suture delivery device from within a cavity of a patient.

7. The suture delivery device of claim 1, wherein each petal of the plurality of petals is teardrop shaped.

8. The suture delivery device of claim 1, wherein at least one petal of the plurality of petals defines a cavity for receiving a needle.

9. The suture delivery device of claim 1, wherein each of the petals of the plurality of petals includes a spring member for biasing each of the petals radially outward.

10. The suture delivery device of claim 1, wherein the support member includes a container for receiving used needles.

11. The suture delivery device of claim 1, wherein the base portion is flexible.

12. The suture delivery device of claim 1, wherein the base portion includes mesh.

13. The suture delivery device of claim 1, wherein the each petal of the plurality of petals is formed of fabric.

14. The suture delivery device of claim 1, further comprising a locking mechanism.

15. The suture delivery device of claim 1, further comprising a trap member on a distal end of at least one petal.

* * * * *